United States Patent [19]
Zern et al.

[11] Patent Number: 5,637,315
[45] Date of Patent: Jun. 10, 1997

[54] TREATMENT OF DISEASE STATES INDUCED BY OXIDATIVE STRESS

[75] Inventors: Mark Zern, Newtown Square; Leaf Huang, Wexford, both of Pa.; Tony Yoa, Knoxville, Tenn.

[73] Assignees: Thomas Jefferson University, Philadelphia; University of Pittsburgh, Pittsburgh, both of Pa.; Roger Williams Medical Center, Providence, R.I.

[21] Appl. No.: 349,129

[22] Filed: Dec. 2, 1994

Related U.S. Application Data

[63] Continuation of Ser. No. 275, Jan. 4, 1993, abandoned.
[51] Int. Cl.$^6$ .......................... A61K 9/127; A61K 9/133
[52] U.S. Cl. ................................. 424/450; 436/829
[58] Field of Search .......................... 424/450; 436/829

[56] References Cited

U.S. PATENT DOCUMENTS

| 4,952,409 | 8/1990 | Bando | 424/450 |
|---|---|---|---|
| 5,047,395 | 9/1991 | Wu | 514/2 |
| 5,162,366 | 11/1992 | Kimoto | 514/460 |
| 5,262,168 | 11/1993 | Leuk | 424/450 |

OTHER PUBLICATIONS

Dai Nakae et al., "Liposome–Encapsulated Superoxide Dismutase Prevents Liver Necrosis Induced by Acetaminophen", *Amer. Journ. of Pathology* 1990, 136(4), 787–795.

Liu and Huang, "Size Homogeneity of a Liposome Preparation is Crucial for Liposome Biodistribution in Vivo", *J. Liposome Res.* 1992, 2, 57–66.

Motoyama, T. et al., "Synergistic Inhibition of Oxidation in Dispersed Phosphatidylcholine Liposomes by a Combination of Vitamin E and Cysteine", *Archives of Biochemistry and Biopohysics* 1989, 270(2), 655–661.

Pak H. Chan, "Antioxidant–Dependent Amelioration of Brain Injury: Role of CuZn–Superoxide Dismutase", *Journ. Neutro.* 1992, 9, S417–S423 Supplement 2.

Poznansky, M. and Juliano, "Biological Approaches to the Controlled Delivery of Drugs: A Critical Review", *Pharmacological Reviews* 1984, 36(4), 277–336.

Roerdink et al., "The Involvement of Parenychmal, Kupffer, and Endothelial Liver Cells in the Hepatic Uptake of Intravenously Injected Liposomes", *Biochemica et Biophysica Acta* 1986, 863, 224–230.

Scherphaf et al., "Targeting of Liposomes to Liver Cells" in *Drug Carrier Systems*, Roerdink and Koon, eds., pp. 281–291, John Wiley & Sons, Ltd., 1989.

Spanjer et al., "Intrahepatic Distribution of Small Unilamellar Liposomes as a Function of Liposomal Lipid Composition", *Biochemica et Biophysica Acta* 1986, 677, 79–89.

Thibeault et al., "Prevention of Chronic Pulmonary Oxygen Toxicity in Young Rats with Liposome–Encapsulated Catalase Administered Intratracheally", *Pediatric Pulmonology*, 11:318–327 (1991).

Pelle, Vitamin E: Biochemistry and Health implications, vol. 570, p. 491, 1989.

Packer, Proc. Soc. Exper. Biol., vol. 220, p. 271, 1992.

Poznansky, Pharmacological Reviews, 36, 1984, p. 227.

Motoyama ABB, 270 #2, p. 655, 1989.

*Primary Examiner*—Gollamudi S. Kishore
*Attorney, Agent, or Firm*—Woodcock Washburn Kurtz Mackiewicz & Norris LLP

[57] ABSTRACT

Liposome carrier systems, methods and pharmaceutical compositions that target an organ preferentially with high concentrations of at least one therapeutic agent utilize a liposome carrier having a lipid membrane and an aqueous space to deliver pharmacologically active agents, such as free radical scavengers and antioxidants, to a target organ such as the liver. At least one free radical scavenger and/or antioxidant and a liposome carrier may be provided to a liver donor prior to harvesting to preserve the liver for transplantation.

4 Claims, 5 Drawing Sheets

TREATMENT OF DISEASE STATES INDUCED BY OXIDATIVE STRESS

INTRODUCTION

This invention was made partially in the course of NIH grant R01 DK41875. The government may have certain rights in this invention.

This is a continuation, of application Ser. No. 08/000,275, filed Jan. 4, 1993, now abandoned.

BACKGROUND OF THE INVENTION

The liver has an essential role in protein metabolism; the degradation of amino acids occurs almost exclusively in the liver. Degradation is a process by which excess amino acids are catabolized and then used for energy or stored as fat. Degradation begins in the liver with deamination of the amino acids. The ammonia formed by deamination is removed from the blood and converted by the liver into urea, which is then excreted by the kidneys and intestines. In severe liver disease or damage, the ammonia that is normally converted to urea and excreted by the liver is allowed to accumulate to toxic levels in the blood.

Hepatocytes are parenchymal liver cells, which are the chief cells of the functional unit of the liver, the liver lobule. In the liver lobule, these cells are arranged hub-like around a central vein, with one side of the polyhedral hepatocyte facing the hepatic sinusoids, the capillary system of the liver, and the other side facing the bile canaliculi. Incoming portal and arterial blood enters the sinusoids, then passes through the liver lobule, where many substances are exchanged between the hepatocytes and the blood. The blood then courses on to the central vein, with special substances filtering into the bile ductules. Endothelial and Kupffer (Littoral) cells form the walls of the sinusoids.

There is considerable evidence that oxidative stress is a contributing factor in the pathogenesis of a variety of liver diseases. Evidence developed over the last several years has suggested that acute liver injury may frequently be caused by free-radical formation, and that these toxic radicals may injure the cell membranes of hepatocytes through lipid peroxidation or by other means. Lipid peroxidation can affect the composition and function of membranes, and ultimately every aspect of cell metabolism. Lipid peroxidation weakens the integrity of the cell membrane, which ultimately kills the cell.

Polyunsaturated fatty acids are particularly sensitive to oxidative stress and are easily damaged in the presence of oxidants such as partially reduced oxygen species (oxygen radicals). Possible sources of the toxic radical species may involve the activity of several liver enzyme systems, including, for example, acetaldehyde oxidase, xanthine dehydrogenase/oxidase, cytochrome p-450IIE1, and oxidases from infiltrating inflammatory cells.

It is believed that free radicals play a role in triggering the fibrosis and cirrhosis cascade. For example, the mechanism of liver damage by carbon tetrachloride is believed to be free radical mediated. The carbon tetrachloride molecule is dehalogenated by cytochrome P-450 to a trichloromethyl free radical. This trichloromethyl free radical adds molecular oxygen to form the trichloromethyl peroxyl radical. This reactive compound removes hydrogen atoms from unsaturated lipids, creating carbon-centered lipid radicals. These lipid radicals add molecular oxygen to produce lipid peroxyl radicals, which induces the process of lipid peroxidation. The membrane damage caused by lipid peroxidation, if not halted, results in the death of the cell due to severe damage to the cell membrane. The cell's natural defenses include scavengers such as vitamin E ($\alpha$-tocopherol), dihydrolipoic acid, and superoxide dismutase. When these scavengers are exhausted, the damage caused by lipid peroxidation is unchecked.

The final stage of many types of liver injury is cirrhosis. Cirrhosis is a chronic liver disease wherein liver function is impaired due to extensive scar tissue. Cirrhosis occurs when the regeneration of new hepatocytes, bile ductules, vascular channels, and reticulin substance alters the normal flow of blood, bile, and hepatic metabolites. Any chemical or organism that causes liver destruction and irregular patchy regeneration will predispose to cirrhosis.

Oxidative stress, in association with ischemia and subsequent reperfusion that occurs with the harvesting and preservation of livers for transplantation, is also a major factor in primary liver graft malfunction. The harvesting of normal donor livers in viable condition is a crucial component of the transplantation process. Livers are considered viable for transplantation after only a limited time ex vivo, despite the introduction of solutions that may help to preserve them. Livers that remain untransplanted for 12 or more hours have a much higher incidence of graft failure secondary to oxidative stress. Even livers that are transplanted after a relatively short period of time following harvesting are subject to oxidative stress.

Liposomes are composed of various phospholipids surrounding an aqueous space which space is usually impermeable to the outside environment. Most liposome formulations have a strong affinity to the liver, and appear to be removed from the liver by the Kupffer cells. Liu and Huang, "Size Homogeneity of a Liposome Preparation is Crucial for Liposome Biodistribution in Vivo," *J Liposome Res.* 2: 57–66, 1992. This affinity is lipid dependent. By varying the size and lipid composition of the liposome, it is possible to alter the affinity to the various populations of cells within the liver itself. Scherphaf, et al., "Targeting of liposomes to liver cells". *Drug Carrier Systems.* Edited by F.H.D. Roerdink and A.M. Koon, 1989 John Wiley & Sons, Ltd., 281–291. Other methods for targeting liposomes to a particular target organ, such as the liver, utilizing antibodies, galactocerebrosides, and/or lipid composition, are known to those skilled in the art. See Roerdink, et al., "The Involvement of Parenchymal, Kupffer, and Endothelial Liver Cells in the Hepatic Uptake of Intravenously Injected Liposomes," *Biochemica et Biophysica Acta,* 1981, 677: 79–89; Spanjer, et al., "Intrahepatic distribution of small unilamellar liposomes as a function of liposomal lipid composition," *Biochemica et Biophysica Acta,* 1986, 863: 224–230.

Currently available treatments for liver disorders are not able to effectively concentrate a therapeutic agent in the target organ. Generally, when a pharmacologically active material is provided to a host, the material is distributed fairly evenly throughout the body, thus diluting its effect at the target organ. To achieve a reasonable effect, a large dose of drug must be administered. Large dosages are a problem when the drug is toxic to other organs. For example, chemotherapeutic agents designed to treat cancer or fulminant infections are limited by the hepatic toxicity of the therapeutic agent.

The present invention overcomes limitations in the prior art by utilizing liposome carrier systems, methods and pharmaceutical compositions that target the liver preferentially with high concentrations of at least one therapeutic agent.

SUMMARY OF THE INVENTION

The present invention provides liposome carrier systems, methods and pharmaceutical compositions that target an organ preferentially with high concentrations of at least one therapeutic agent. Such carriers, methods and compositions utilize a liposome to deliver pharmacologically active agents, such as free radical scavengers and antioxidants, to a target organ such as the liver.

DETAILED DESCRIPTION OF THE INVENTION

It has been found that liposomes may be used to preferentially concentrate pharmacologically active agents, such as free radical scavengers and antioxidants, in the liver. In the liposome carrier systems, pharmaceutical compositions, and methods of the present invention, a liposome carrier having a lipid membrane and an aqueous space is utilized to deliver at least one therapeutic agent to the liver. In certain aspects of the invention, the liposome carriers are provided with antibodies or galactocerebrosides or comprise a specified lipid composition known to have an affinity for the liver or for certain populations of cells within the liver. By varying the size and lipid composition of the liposome, it is possible to alter the bio-distribution of a therapeutic agent among the various populations of cells within the liver itself. Such targeting may be accomplished through intravenous administration of the liposome carrier and therapeutic agent.

The present invention provides pharmaceutical compositions for the treatment of liver disorders. Such compositions comprise at least one free radical scavenger or antioxidant and a liposome carrier having a lipid membrane and an aqueous space. Suitable free radical scavengers or antioxidants for use in such compositions include, for example, α-tocopherol, ascorbic acid 6-palmitate, dihydrolipoic acid, and butylated hydroxytoluene. The liposome carrier may comprise, for example, egg phosphatidylcholine and cholesterol.

In the pharmaceutical compositions of the present invention, the aforementioned fat soluble therapeutic agents are incorporated into the lipid membrane of the liposome carrier. Other water soluble therapeutic agents may be enclosed within the aqueous space of the liposome carrier. The liposome carrier may be provided with antibodies or galactocerebrosides, or may comprise a specified lipid composition known to have an affinity for the liver or for certain populations of cells within the liver.

One aspect of this invention provides a method for protecting the liver of a host from free radical-mediated cell damage comprising the step of administering to the host at least one free radical scavenger or antioxidant selected from the group comprising α-tocopherol, ascorbic acid 6-palmitate, dihydrolipoic acid, and butylated hydroxytoluene, and a liposome carrier having a lipid membrane and an aqueous space.

Figure 1:
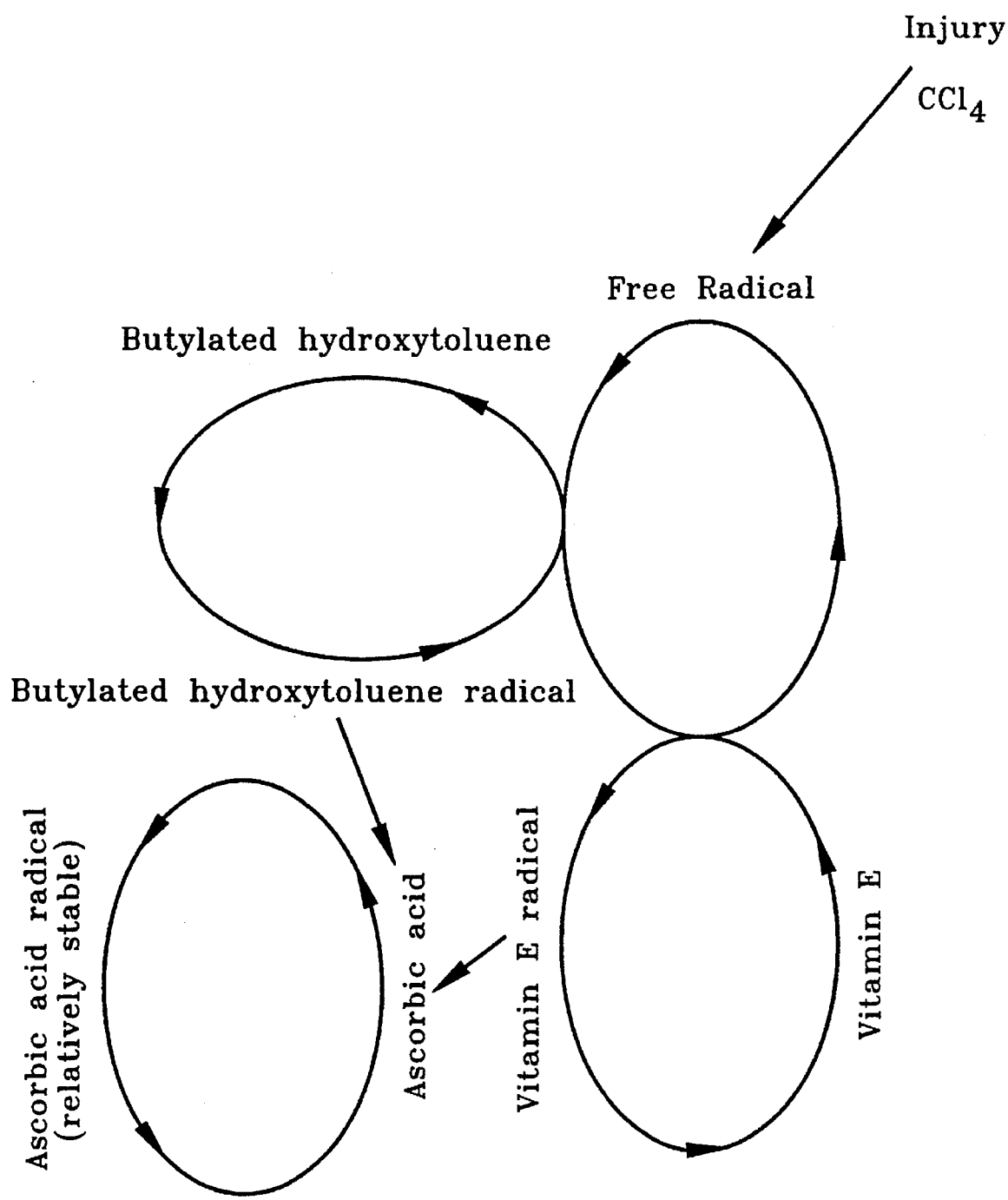
FIG. 1 is a diagram of the hypothesized cycle of free radical quenching.

In a preferred method for protecting the liver of a host from free radical-mediated cell damage, α-tocopherol and ascorbic acid 6-palmitate and a liposome carrier are administered to the host. These compounds are preferred because these compounds complement each other in the hypothesized cycle of free radical quenching (See FIG. 1).

Another aspect of this invention provides methods for concentrating a therapeutic agent in the liver comprising administering the therapeutic agent with a liposome carrier having a lipid membrane and an aqueous space. For example, therapeutic agents including α-tocopherol, ascorbic acid 6-palmitate, dihydrolipoic acid, and butylated hydroxytoluene, free radical scavengers, may be concentrated in the liver by administering the therapeutic agent intravenously with a liposome carrier. Other examples of therapeutic agents which may be administered with a liposome carrier include antibodies, for example antibidies to TGF-beta, receptor antagonists, such as IL-1 receptor antagonists, nucleic acids, such as antisense to liver genes including, for example, the alpha-1 anti-trypsin gene where the oligonucleotides may be in viral vectors, and monomethyl arginine.

In the pharmaceutical compositions and methods of the present invention, therapeutic agents that are fat soluble may be incorporated into the lipid membrane of the liposome carrier. Water soluble therapeutic agents may be enclosed within the aqueous space of the liposome carrier.

Liposome carrier systems for concentrating a therapeutic agent in a target organ are also provided by this invention. For water soluble therapeutic agents, such carrier systems comprise a liposome having a lipid membrane and an aqueous space and a water soluble therapeutic agent enclosed within the aqueous space of the liposome. For fat soluble therapeutic agents, such carrier systems comprise a liposome having a lipid membrane and an aqueous space and a lipid soluble therapeutic agent incorporated into the lipid membrane of the liposome.

In the pharmaceutical compositions, liposome carrier systems, and methods of the present invention, the liposome carriers may comprise, for example, egg phosphatidylcholine and cholesterol. The liposome carriers may be provided with antibodies or galactocerebrosides, or may comprise a specified lipid composition known to have an affinity for the liver or for certain populations of cells within the liver.

In preferred embodiments, the liposome carrier is about 100 nm in diameter and comprises about 20 mg egg phosphatidylcholine and about 6.6 mg cholesterol (molar ratio 1.5:1).

The liposome carrier systems, pharmaceutical compositions and methods described herein may be utilized for therapy of other disorders induced by oxidative stress. For example, the liposome carrier system may be used for the treatment of ischemic cerebral vascular accidents. Acute decreased perfusion of the brain is associated with ischemic injury. If the blockage is complete, ischemic necrosis would occur over a short period of time. However, if the blockage were only partial, there would be regions of relative ischemia. These regions of relative ischemia may also occur in the tissue surrounding a necrotic region. This condition might be well suited for therapy with a free radical scavenger such as vitamin E. The liposome carriers may be injected directly into the cerebral spinal fluid, thereby allowing the liposomes to target the brain. This type of targeting is not possible via the vascular system.

Vitamin E-loaded liposomes may be also used in the therapy of acute myocardial infarction or myocardial ischemia. These ischemic cardiac events cause regions of relative ischemia that may be saved if injury caused by oxidative stress were limited. Cardiac catheterization and radionucleotide scanning may be used during an ischemic event to delineate the region of ischemia. The liposomes could be injected directly by catheterization to the region supplied by the partially occluded vessel, thereby targeting the liposomes to the involved area.

The liposome carrier system may be used for a variety of therapeutic agents that are not free radical scavengers or antioxidants. More than one agent may be employed in a liposome, forming a "cocktail". For example, one might want to include an antioxidant plus an hepatoprotective agent such as prostaglandin $E_2$. Or one might employ an antioxidant plus an antibody to an injurious growth factor, such as transforming growth factor-$\beta$. The targeting properties of the liposomes would help limit the side effects of toxic drugs.

Liposomes containing free radical scavengers, such as vitamin E, could be employed in the preservation of donor livers for transplantation. Prior to the harvesting of the liver, for example, about two hours prior to harvesting, at least one free radical scavenger or antioxidant and a liposome carrier could be given by normal intravenous infusion. Those skilled in the art recognize methods for determining the amount of free radical scavenger and/or antioxidant necessary to provide protective action lasting for the entire time between harvesting and implantation into the recipient. Moreover, the constituents of the liposome would also act as hepatoprotective agents during the operation and in the immediate postoperative period.

Further variations and modifications of the aforementioned can, of course, be made without departing from the spirit and scope of the invention as disclosed herein, and those skilled in the art will recognize multiple utilizations of the present invention that are within the scope of this disclosure.

EXAMPLES

Example 1

The acute carbon tetrachloride mouse model, which mimics acute hepatotoxicity, was used to evaluate the efficacy of treatment with liposomes containing various antioxidants and free radical scavengers. The validity of the acute model in mice was first tested.

Groups of three mice were injected intraperitoneally with various amounts of carbon tetrachloride. The concentrations used were 22 µl/kg, 88 µl/kg, and 176 µl/kg. The mice were sacrificed 18 hours post injection, and blood serum was analyzed for transaminases. Liver damage was gauged by the amount of serum transaminases (serum glutamate pyruvate transaminase (SGPT) and serum glutamate oxasoacetate transaminase (SGOT)) released into the blood.

Figure 2:
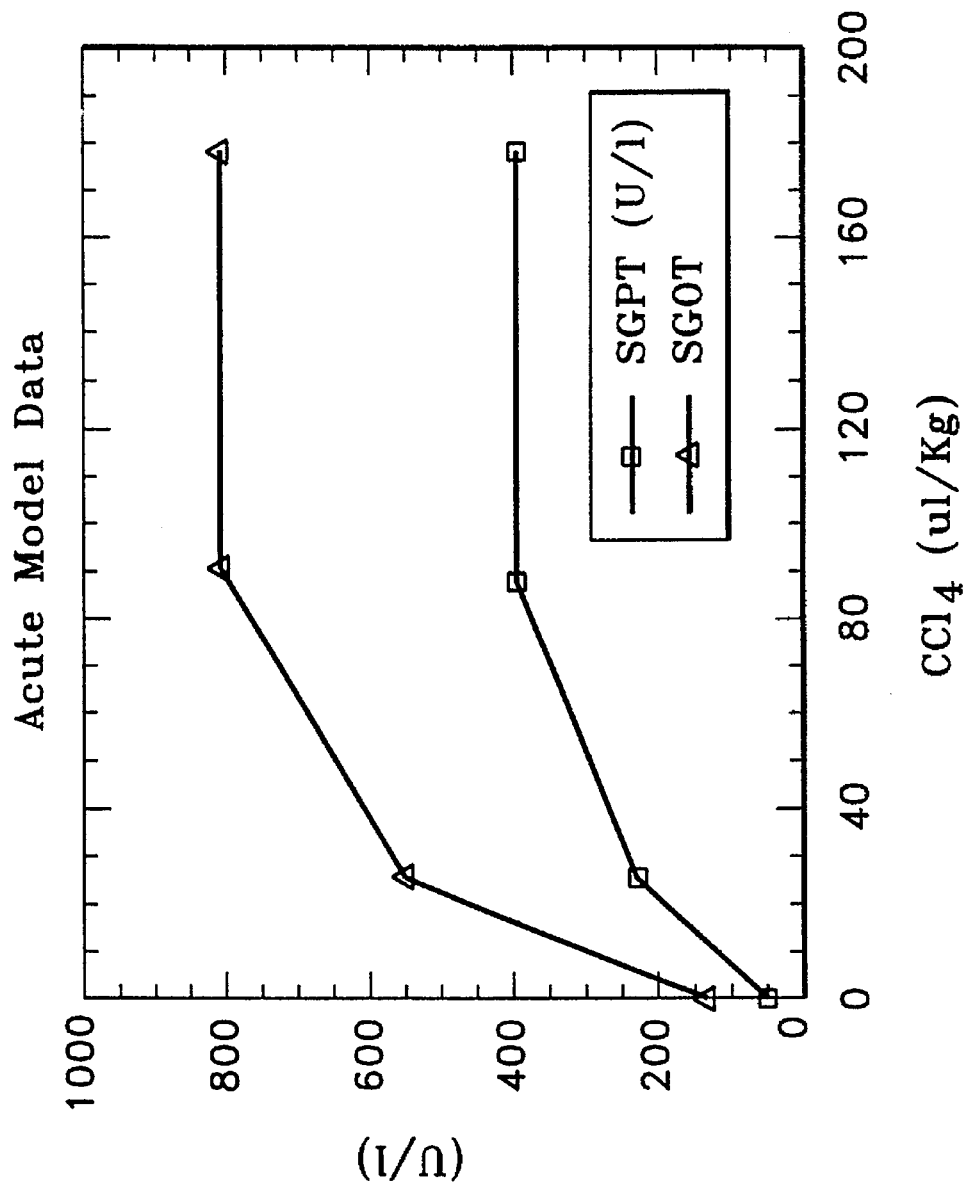
FIG. 2 illustrates the effect of carbon tetrachloride injections on the serum SGPT and SGOT of mice.

When the carbon tetrachloride in quantities greater than 22 µg/kg was injected, the amount of transaminases became too high to be read without dilution. The SGPT and SGOT levels were greater than 800 and 400 U/L respectively in all cases, except for 22 µg/kg. See FIG. 2.

From the data derived from this and other similar experiments, it was determined that the optimal amount of carbon tetrachloride to be injected was about 18–40 µg/kg.

Example 2

Liposomes were prepared by the extrusion method. Phospholipid (egg phosphatidylcholine), cholesterol (molar ratio 1.5:1), and selected free radical scavengers were dried to a film in a test tube. Phosphate buffered saline (pH 7.5) was added to make a lipid concentration of 25 mg/ml. The mixture was allowed to hydrate for four hours with occasional vortexing. Before extrusion, the suspension was sonicated briefly in a bath type sonicator. The liposomes were then extruded through a 0.05 nm polycarbonate filter.

CF-1 mice (at least 3 per group) were injected intravenously with a preparation which combined a liposome with vitamin E, butylated hydroxytoluene, or ascorbic acid 6-palmitate or vitamin E succinate. Total lipid was 11.3 mg.

Two hours later, the mice were injected intraperitoneally (i.p.) with 1.1 µl of carbon tetrachloride in vegetable oil. After twenty hours, the mice were sacrificed. The livers were removed for histological study. Blood was also taken and the serum was analyzed for serum transaminase levels.

E=vitamin E, ES=vitamin E succinate, BHT=butylated hydroxytoluene, c=vitamin C.

Figure 3:
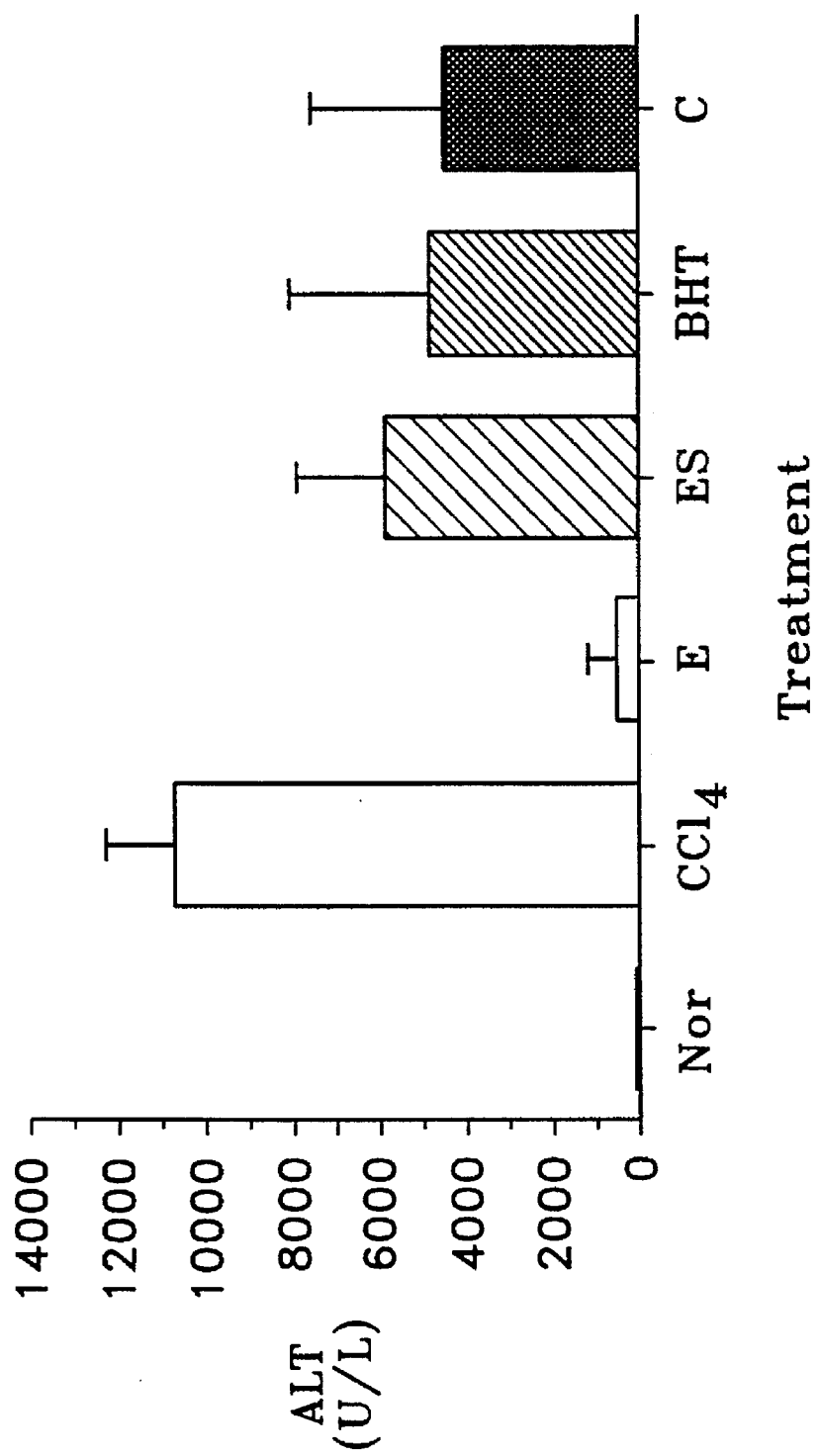
FIG. 3 illustrates the effects of liposomes containing a variety of oxygen-radical scavengers on liver injury caused by a sublethal dose of carbon tetrachloride.
Figure 4:
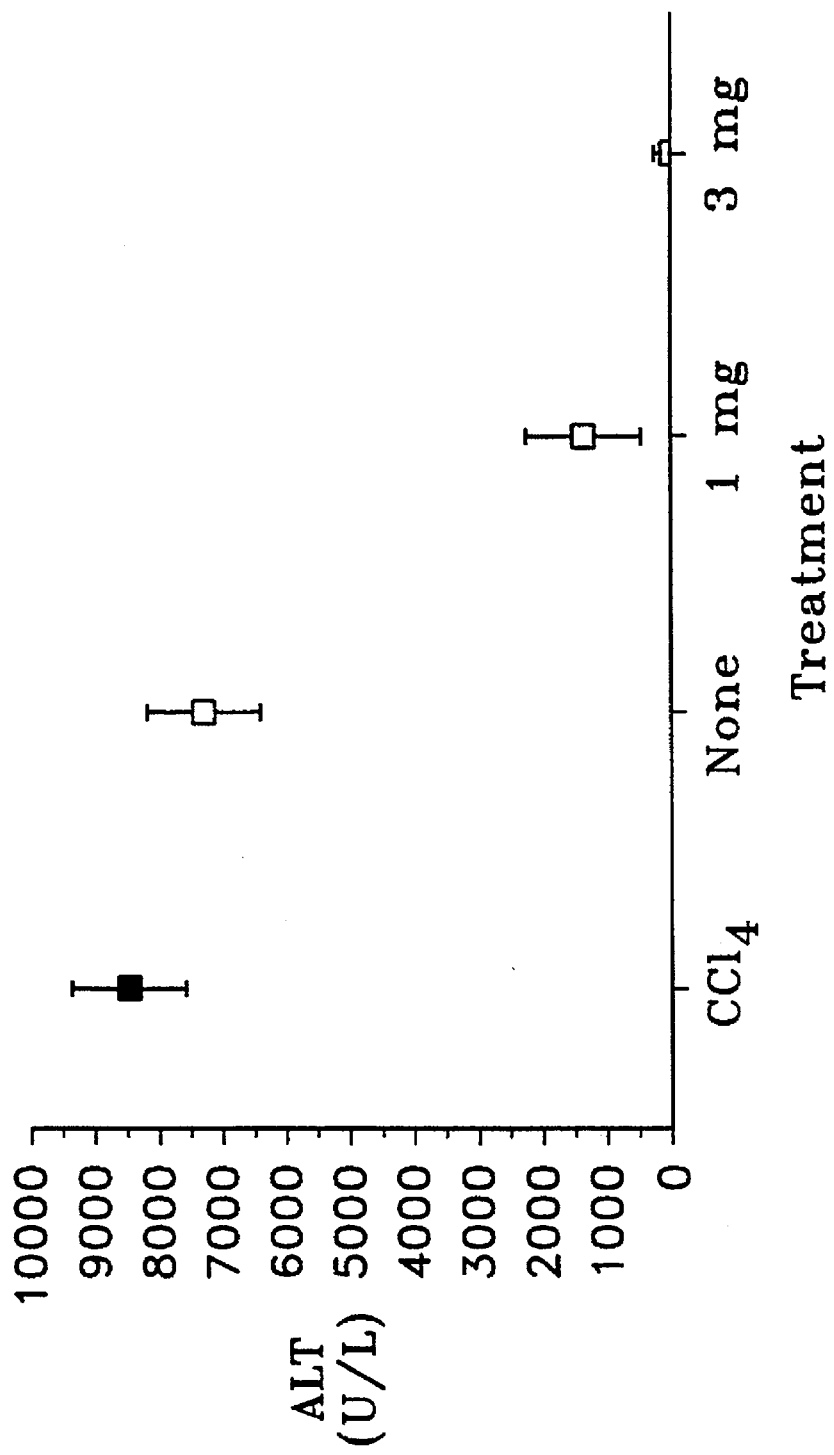
FIG. 4 illustrates a dose dependent curve which demonstrates that liposomes alone do not significantly inhibit the liver injury induced by carbon tetrachloride, but that liposomes containing increasing amounts of Vitamin E do inhibit the sublethal injury.
Figure 5:
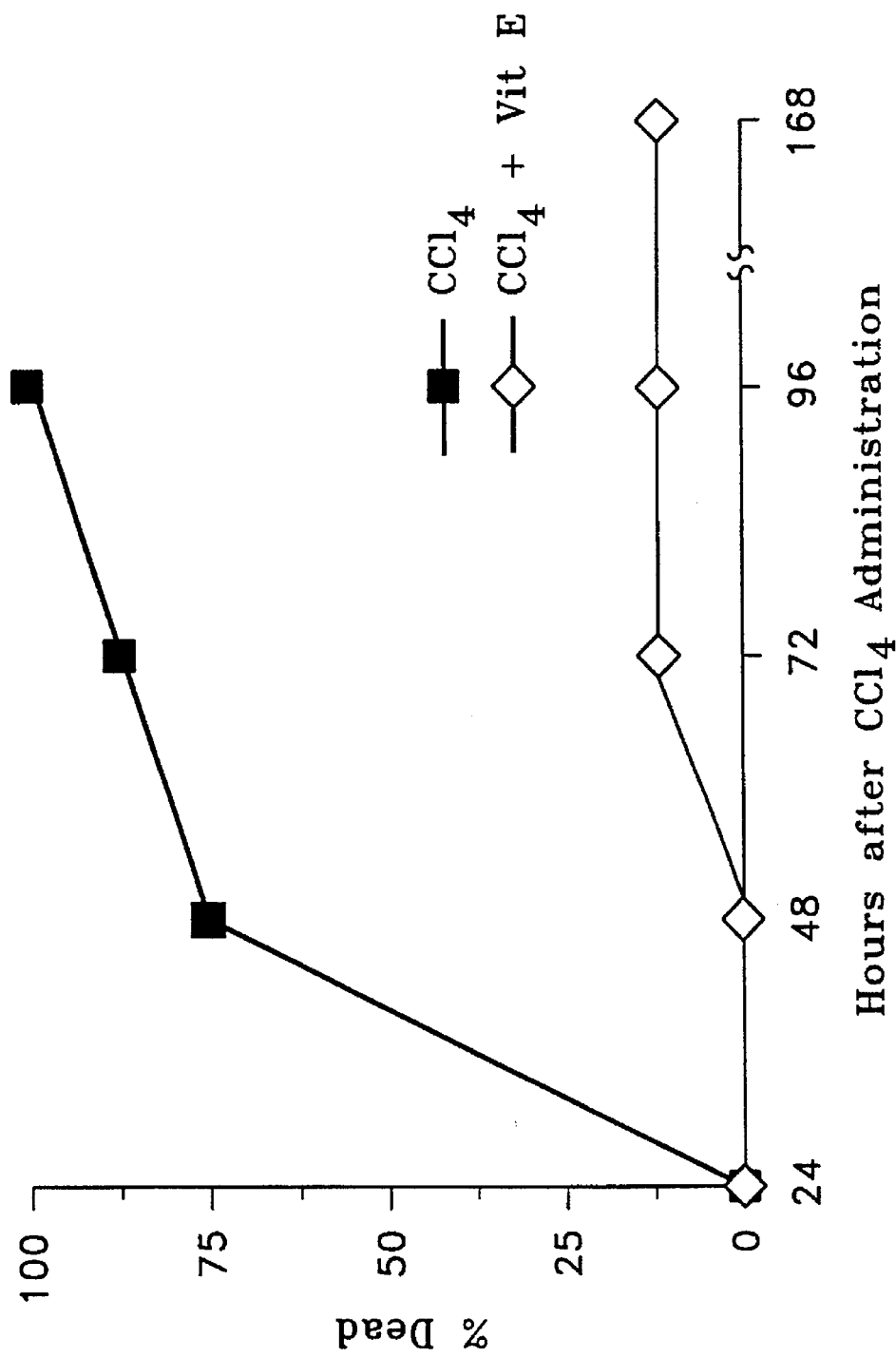
FIG. 5 illustrates that liposomes containing vitamin E markedly reduce the effects of a lethal dose of carbon tetrachloride.

As shown in FIG. 3, vitamin E was much more efficient in reducing hepatic injury, as measured by a reduction in ALT (ALT=SGPT). These, and other similar experiments suggest that the preferred oxygen radical scavenger composition of the liposomes is vitamin E alone.

Example 3

Liposomes were prepared as described for Example 2. In this experiment, one group of animals was injected with liposomes without vitamin E, while two others groups were injected with liposomes containing increasing amounts of vitamin E. All groups were then treated intraperitoneally with carbon tetrachloride. The vitamin E-treated mice had much less injury as measured by ALT levels.

Example 4

Liposomes were prepared as described for Example 2. In this experiment, the first group (8 mice) received a lethal dose of carbon tetrachloride without any liposome therapy. All the animals died. The second group (8 mice) received liposomes containing vitamin E, and then two hours later received the lethal dose of carbon tetrachloride. Only one of the eight died in the treated group.

We claim:

1. A method for protecting the liver of a host from free radical-mediated cell damage comprising the step of intravenously administering to said host a pharmaceutical composition consisting essentially of at least one free radical scavenger or antioxidant selected from the group consisting of α-tocopherol, ascorbic acid 6- palmitate, dihydrolipoic acid, and butyl hydroxytoluene, and a liposome carrier for concentrating said scavenger or antioxidant in the liver, said liposome carrier having a lipid membrane and being up to about 100 nm in diameter, said scavenger or antioxidant being encapsulated in said liposome carrier.

2. The method of claim 1 wherein said at least one free radical scavenger or antioxidant is incorporated into said lipid membrane of said liposome carrier.

3. A method for protecting the liver of a host from free radical-mediated cell damage comprising the step of intravenously administering to said host a pharmaceutical composition consisting essentially of at least one free radical scavenger or antioxidant selected from the group consisting of α-tocopherol, ascorbic acid 6-palmitate, dihydrolipoic acid, and butylated hydroxytoluene, and a liposome carrier for concentrating said scavenger or antioxidant in the liver, said liposome carrier having a lipid membrane and being up to about 100 nm in diameter, said scavenger or antioxidant being encapsulated in said liposome carrier, wherein said liposome carrier is further provided with compounds selected from the group consisting of antibodies, prostaglandin $E_2$, and galactocerebrosides.

4. A method for protecting the liver of a host from free radical-mediated cell damage comprising the step of intravenously administering to said host a pharmaceutical composition consisting essentially of α-tocopherol and a liposome carrier for concentrating said α-tocopherol in the liver, said liposome carrier having a lipid membrane and being up to about 100 nm in diameter, and said α-tocopherol being encapsulated in said liposome carrier.

* * * * *